United States Patent [19]

Hofeldt

[11] Patent Number: 5,398,085
[45] Date of Patent: Mar. 14, 1995

[54] DEVICE FOR TESTING VISION POTENTIAL

[76] Inventor: Albert J. Hofeldt, 200 E. 57th St., New York, N.Y. 10022

[21] Appl. No.: 61,967

[22] Filed: May 14, 1993

[51] Int. Cl.⁶ ............................................. A61B 3/02
[52] U.S. Cl. .................................. 351/243; 351/244; 351/246
[58] Field of Search ............... 351/200, 243, 244, 246, 351/222, 239

[56] References Cited

U.S. PATENT DOCUMENTS

| | | | |
|---|---|---|---|
| 666,557 | 1/1901 | Reich et al. | 351/243 |
| 726,101 | 4/1903 | Reich et al. | 351/243 |
| 5,054,908 | 10/1991 | Katsumi et al. | 351/239 |

*Primary Examiner*—William L. Sikes
*Assistant Examiner*—Huy Mai
*Attorney, Agent, or Firm*—Rosenman & Colin

[57] ABSTRACT

A device for testing vision potential of humans comprises an enclosure containing two transparent areas through one surface, two pairs of rollers, means for turning one of the rollers, a length of material fitted around the two pairs of rollers in snug engagement therewith so that by operating the means for turning one of the rollers the material moves around the two pairs of rollers, said material having a series of vision testing lines of indicia sized to test visual acuity from 20/20 to 20/200, each of said lines being visible in one area and each of said lines having on the material and visible through the other area markings from 20/20 to 20/200. Two sources of illumination are disposed within the enclosure, one illumination source being disposed in a position to illuminate the line of indicia and the other being positioned to illuminate the series of numbers from 20/20 to 20/200. Means for providing sufficient energy to the illumination means to enable them to provide illumination and means for positioning the person to be tested at the desired from the device are provided. The device has particular applicability for determining the vision potential of humans having a cataract in one or both eyes which through utilizing a device with a pinhole through which the person to be tested views the lines of indicia one can accurately determine the visual acuity which will be achieved following cataract surgery.

22 Claims, 4 Drawing Sheets

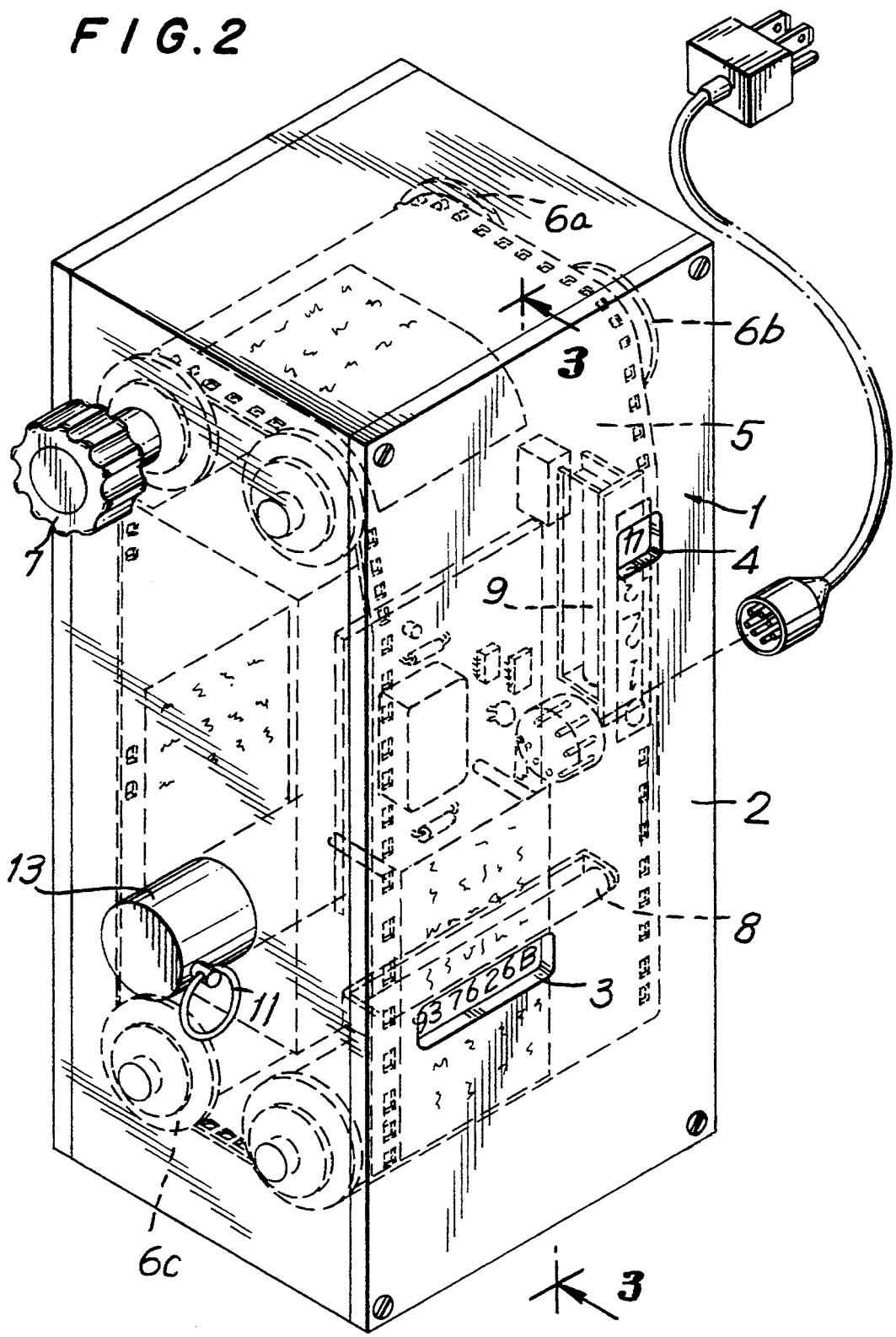

DEVICE FOR TESTING VISION POTENTIAL

The present invention is concerned with a device for accurately testing vision and has particular applicability for testing vision potential following cataract surgery for people having cataracts in one or both eyes prior to the surgery.

When there is a vision loss, determining the vision potential after surgery is an important goal of all eye care specialists. Cataracts are a common and correctable cause of vision loss. A cataract is the result of opacification of the lens of the eye. Accurate prediction of the vision potential of patients considered for cataract surgery is a challenge to the ophthalmic surgeon. According to Sadun and Libondi (Amer. J. Ophthalmology 110:710–712, 1990), cataracts can reduce 90% of the light from being transmitted through the lens of the eye. If a sufficient quantity of focused light penetrates the cataract an accurate measurement of the visual ability of the retina is possible.

The present invention is based on the provision of a device which contains a brightly illuminated series of lines of indicia which are capable of determining visual acuity from 20/20 to 20/200. When vision loss is due to a mild or moderate opacification in the ocular media, viewing the brightly illuminated indicia in my device can accurately predict the visual potential of the eye being tested after surgery has been performed. In patients with more severe clouding of the ocular media, a device having a pinhole placed in the line of sight can improve focusing while viewing the illuminated lines of indicia. In general, the stenopaeic hole (pinhole) greatly improves visual defects due to refractive anomalies, to a less extent than those due to abnormalities in the media, but does not ameliorate and may even aggravate those due to faulty perception (Duke-Elder, Textbook of Ophthalmology, Vol. IV). The pinhole places the eye in an almost universal depth of focus and allows the near point to be brought close while maintaining image clarity. As the distance of the image decreases the magnification of the retinal image increases (Lebensohn, Amer. J. Ophthalmology 33:1612–1614, 1950). To avoid image magnification that would overestimate the potential visual ability, the working distance for near vision testing must be maintained at a standard distance. While the pinhole improves the focusing, the small aperture of the pinhole reduces the illumination and must be compensated by supplemental lighting of the lines of indicia to ensure the fullest utilization of the pinhole acuity.

Techniques for measuring visual function in the presence of opacities using vision Snellen letters have been described by Cavonius and Hilz (Investigative Ophthalmology 12:933–935, 1973) and by Minkowski, Palese and Guyton (Ophthalmology 90:1360–1368). Both of these reports describe instruments that project a vision chart into the subject's eye and onto the retina. The instant invention differs from those in that the person to be tested views an intensely illuminated line of indicia preferably of letters held at the appropriate distance to determine near vision with or without the aid of a pinhole placed before the person's eye. This has never been described or suggested in any of the literature.

More particularly, my invention is a device which comprises an enclosure containing two transparent areas, for example, windows, through one surface, two pairs of rollers, one pair of which is disposed within the upper part of the enclosure and the second pair of which is disposed within the lower part of the enclosure, means for turning one of the rollers, a length of material fitted around the two pairs of rollers in snug engagement therewith so that by operating the means for turning one of the rollers the material moves around the two pairs of rollers, said material having a series of vision testing lines of indicia sized to test visual acuity from 20/20 to 20/200, each of said lines being visible through one area and each of said lines having on the material and visible through the other area markings from 20/20 to 20/200 which is visible to the person conducting the test thereby indicating the line which is visible to the person being tested. Two sources of illumination are disposed within the enclosure, one illumination source being disposed in a position to illuminate the line of indicia visible through the first area and the other being positioned to illuminate the series of numbers from 20/20 to 20/200 visible through the second area, means for providing sufficient energy to the illumination means to enable them to provide sufficient illumination and means for positioning the person to be tested at the desired distance from the device.

According to a further embodiment the lines of indicia are lines of letters.

According to a further embodiment each of the lines of letters comprise a line having a letter recognition average of at least 85%.

According to a further embodiment the material on which the indicia are placed is a thin transparent film.

According to a further embodiment the means for turning one of the rollers comprises automated means.

According to a further embodiment a hand-held instrument having a pinhole through which the person to be tested may view the illuminated line of indicia is provided.

The present invention also comprises a method of testing the vision potential of a human which comprises placing the person to be tested in front of the device of the present invention, positioning the patient the proper distance from the device by using the means for positioning the person, illuminating the two sources of illumination, and using the means for turning one of the rollers to determine the person's visual acuity.

According to a further embodiment, the lines of indicia are lines of letters.

According to a further embodiment, the lines of letters comprise a line having a letter recognition average of at least 85%.

According to a further embodiment, the material on which the indicia are placed is a thin transparent film.

According to a further embodiment, the means for turning one of the rollers comprises automated means.

According to a further embodiment the vision potential following surgery is determined for a person having a cataract in at least one eye which comprises providing the patient with a device having a pinhole therethrough through which the patient views the lines of indicia as displayed on the device of the present invention.

The present invention may be more readily understood by reference to the drawings and the following more detailed description.

FIG. 2 is an enlarged view of FIG. 1 as seen through the outer enclosure members.

My device is portable, illuminated and rechargeable so it may be easily moved to accommodate the person to be tested. According to one embodiment of my invention, the letters and/or numbers used are standardized sizes and are photographed on perforated 70 mm high-contrast copy film.

The letters and/or numbers used for testing visual acuity are presented in two formats: white images with a black background and black images with a white background. The image sizes can be gauged for any working distance for determining visual acuity from 20/20 to 20/200. In a preferred embodiment of the present invention, letters are used and each line has an average letter recognition of 85% which means that a person with 20/20 vision will correctly recognize the letters 85% of the time.

Figure 5:
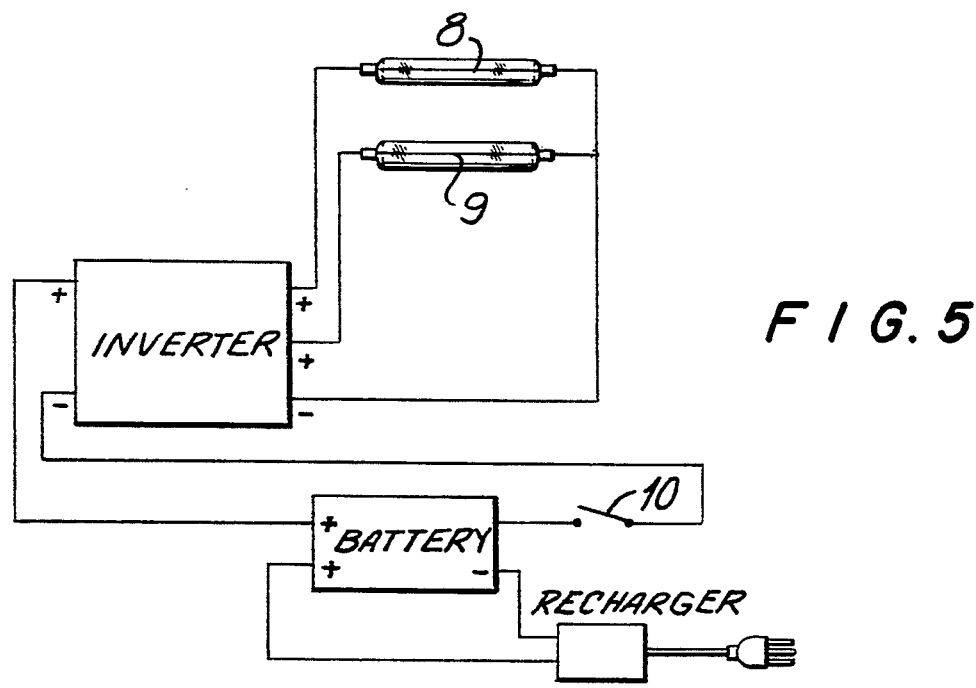
FIG. 5 is a diagrammatic view of the two illumination means and the energy source therefor.
Figure 3:
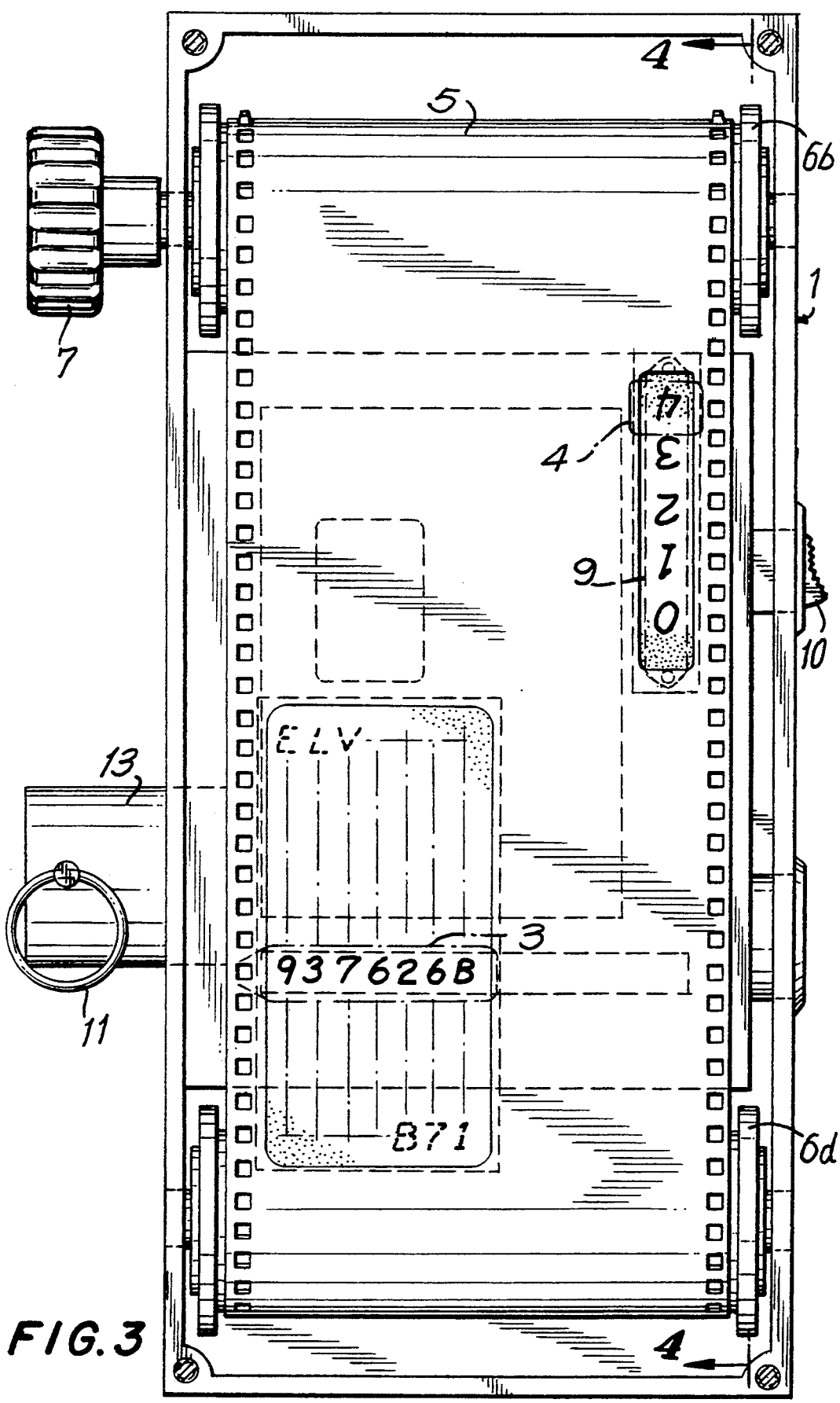
FIG. 3 is a view taken along line 3—3 of FIG. 2.
Figure 4:
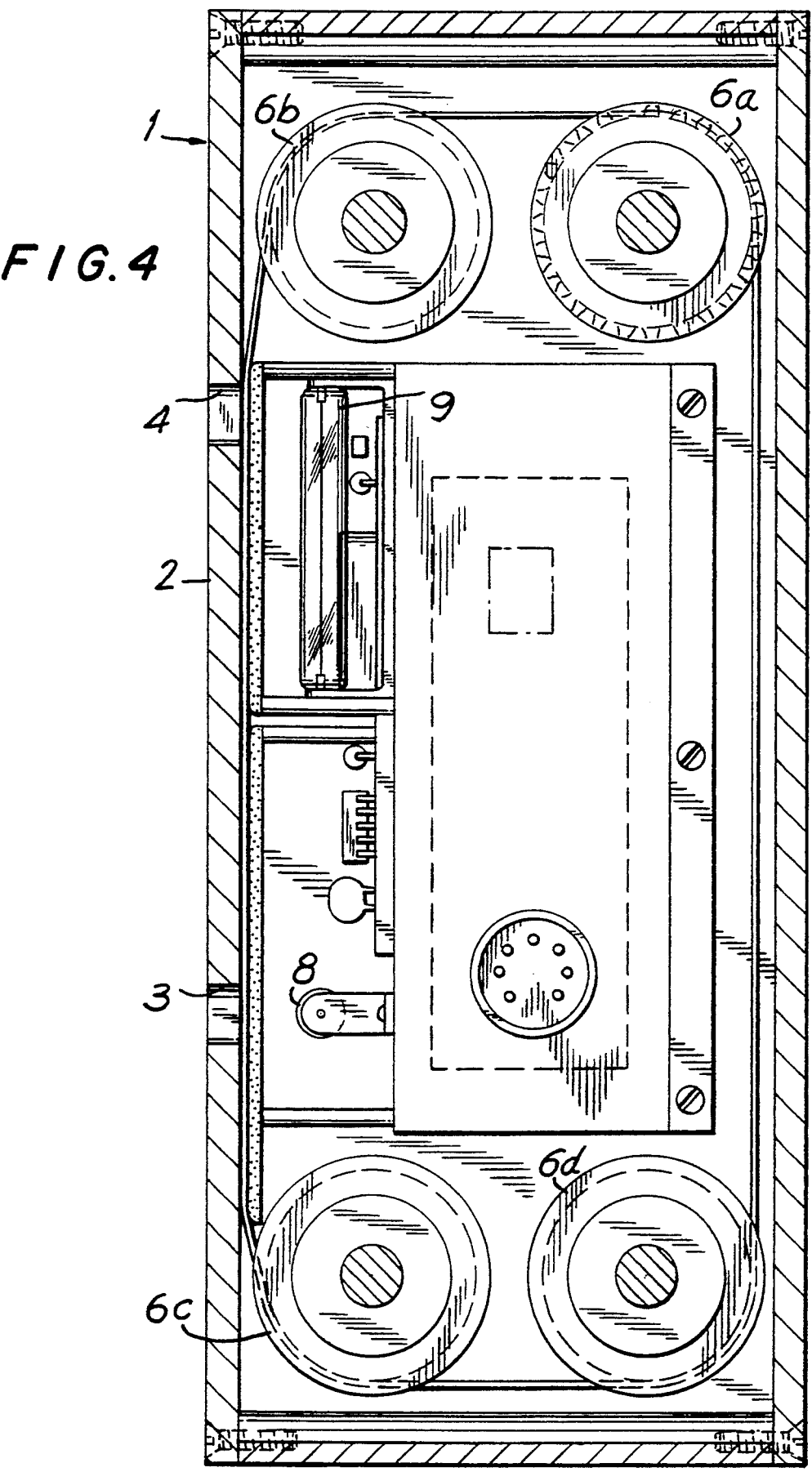
FIG. 4 is a side view.

With more particular reference to the drawings, my device comprises an enclosure 1 having a front surface 2 through which are transparent areas or windows 3 and 4. The letters and/or numbers of standardized sizes are visible to the person to be tested through area 3 and a smaller area on the top surface shows numbers corresponding with the size of the images which the patient views. As shown in more detail in FIGS. 2 and 3, standardized letters and numbers are photographed on perforated 70 mm high-contrast copy film 5 which is mounted as a continuous loop over four rollers 6a, 6b, 6c and 6d. Roller 6a is fitted with suitable means for turning the roller and hence the film such as, for example, knob 7. The film 5 is illuminated behind area 3 by illumination means 8 and the smaller area on the top surface 4 is illuminated by suitable illumination means such as light 9. Lights 8 and 9 are connected to suitable energy sources such as shown diagrammatically in FIG. 5 On/off switch 10 turns the lights on and off as desired. Ring 11 is connected to retractable line 12 which is extendable from member 13. This length of line is 14–16 inches long and allows the person to be tested to be positioned the proper distance away from my device for testing purposes.

The illumination sources 8 and 9 are preferably two miniature fluorescent bulbs mounted beneath the film plane with ground-glass or diffusion tape interposed between the lights and the film. One bulb is preferably mounted parallel and central to area 3 and the other is mounted perpendicular and central to area 4.

The bulb may, for example, be connected to a transformer which is connected to a 6-volt rechargeable battery.

TESTING METHOD

Figure 1:
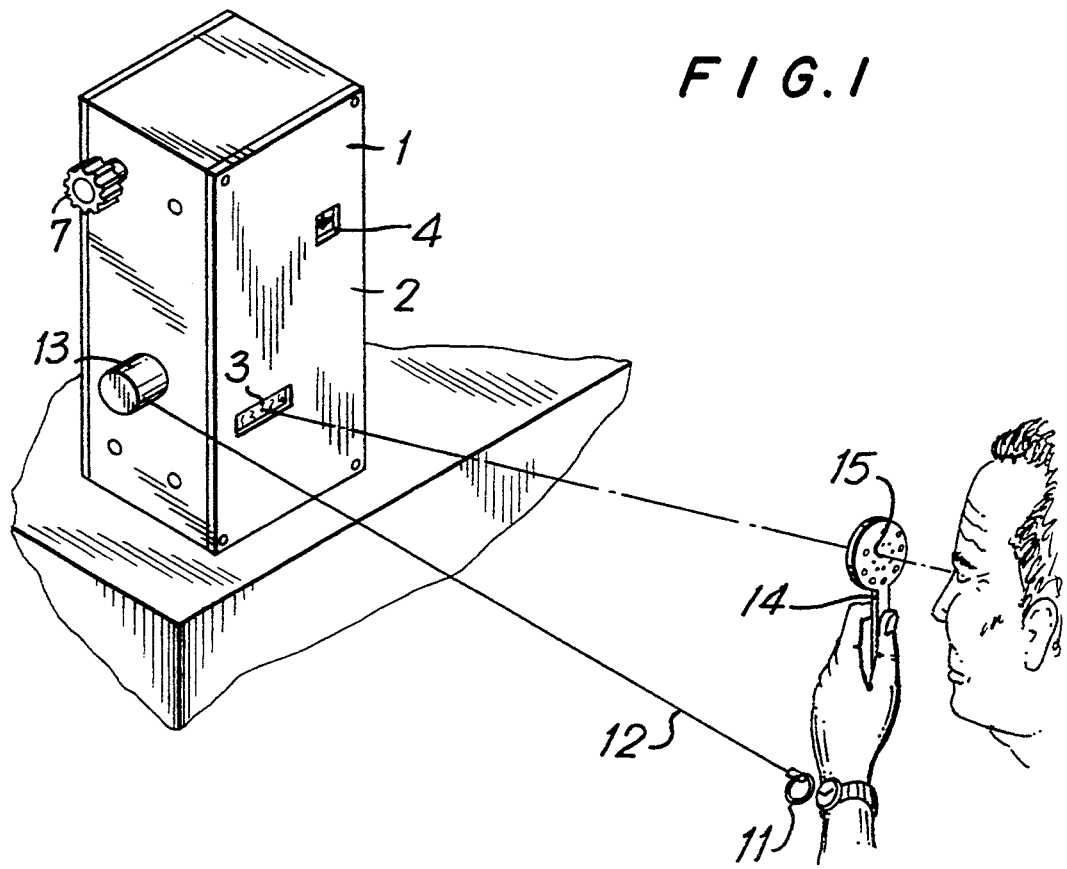
FIG. 1 shows my device placed on a suitable viewing surface.

The person to be tested is positioned at a distance of 14–16 inches from the device as shown in FIG. 1. The patient then views the standard sized numbers and/or letters visible through the brightly illuminated rectangular area 3. The eyes are tested separately while wearing lenses that fully correct the vision for near reading. The size of the numbers and/or letters are progressively reduced in size by turning knob 7 which in turn moves the film plane containing the numbers and/or letters. If 20/20 near acuity is not achieved, then a device 14 having a pinhole 15 therethrough is placed near the corrective lenses in the line of sight and the testing procedure is repeated to determine the best visual acuity.

Based on this testing procedure utilizing the device of my present invention, I have been able to accurately predict the near vision acuity which may be achieved following cataract surgery.

My device may also be used for determination and screening of near vision acuity in patients other than those having cataracts.

Other and further uses of my invention will be more fully appreciated by those skilled in the art by reference to the above description, the drawings and the claims appended hereto.

What is claimed is:

1. A device for testing near vision potential in humans which comprises an enclosure containing two transparent areas through one surface, two pairs of rollers, one pair of which is disposed within the upper part of the enclosure and the second pair of which is disposed within the lower part of the enclosure, means for turning one of the rollers, a length of material fitted around the two pairs of rollers in snug engagement therewith so that by operating the means for turning one of the rollers the material moves around the two pairs of rollers, said material having a series of vision testing lines of indicia sized to test near visual acuity from 20/20 to 20/200, each of said lines being visible through one area and each of said lines having on the material and visible through the other area markings from 20/20 to 20/200 which is visible to the person conducting the test thereby indicating the line which is visible to the person being tested, two sources of illumination disposed within the enclosure one of which is intense, the source of intense illumination is disposed in a position to illuminate the line of indicia and the other source is positioned to illuminate the series of numbers from 20/20 to 20/200, means for providing sufficient energy to the illumination sources to enable them to provide intense and normal illumination respectively and means for positioning the person to be tested for near vision potential at the desired distance from the device.

2. A device according to claim 1 wherein the lines of indicia are lines of letters.

3. A device according to claim 2 wherein each of the lines of letters comprises a line having a letter recognition average of at least 85%.

4. A device according to claim 1 wherein the material is a thin transparent film.

5. A device according to claim 1 wherein the means for turning one of the rollers comprises automated means.

6. A method for testing the near vision potential of a human which comprises placing the person whose near vision potential is to be tested in front of an enclosure containing two transparent areas through one surface, two pairs of rollers, one pair of which is disposed within the upper part of the enclosure and the second pair of which is disposed within the lower part of the enclosure, means for turning one of the rollers, a length of material fitted around the two pairs of rollers in snug engagement therewith so that by operating the means for turning one of the rollers the material moves around the two pairs of rollers, said material having a series of vision testing lines of indicia sized to test near visual acuity from 20/20 to 20/200, each of said lines being visible through one area and each of said lines having on the material and visible through the other area markings from 20/20 to 20/200 which is visible to the person conducting the test thereby indicating the line which is visible to the person being tested, two sources of illumination disposed within the enclosure one of which is intense, the source of the intense illumination is disposed in a position to illuminate the line of indicia and the other source is positioned to illuminate the series of numbers from 20/20 to 20/200, and having means for providing sufficient energy to the illumination sources to enable them to provide intense and normal illumination respectively and means for positioning the person whose near vision potential is to be tested at the desired distance from the device, positioning the person the proper distance from the device to test near vision potential by using the means for positioning the person, illuminating the two sources of illumination, and using the means for turning one of the rollers to determine the person's near visual acuity while the person views the intensely illuminated indicia.

7. A method according to claim 6 wherein the lines of indicia are lines of letters.

8. A method according to claim 7 wherein each of the lines of letters comprises a line having a letter recognition average of at least 85%.

9. A method according to claim 6 wherein the material is a thin transparent film.

10. A method according to claim 6 wherein the means for turning one of the rollers comprises automated means.

11. A method according to claim 6 for determining the vision potential for a person having a cataract in at least one eye.

12. A device for testing near vision potential in humans which comprises, in combination, an enclosure containing two transparent areas through one surface, two pairs of rollers, one pair of which is disposed within the upper part of the enclosure and the second pair of which is disposed within the lower part of the enclosure, means for turning one of the rollers, a length of material fitted around the two pairs of rollers in snug engagement therewith so that by operating the means for turning one of the rollers the material moves around the two pairs of rollers, said material having a series of vision testing lines of indicia sized to test near visual acuity from 20/20 to 20/200, each of said lines being visible through one area and each of said lines having on the material and visible through the other area markings from 20/20 to 20/200 which is visible to the person conducting the test thereby indicating the line which is visible to the person being tested, two sources of illumination disposed within the enclosure one of which is intense, the source of intense illumination is disposed in a position to illuminate the line of indicia and the other source is positioned to illuminate the series of numbers from 20/20 to 20/200, means for providing sufficient energy to the illumination sources to enable them to provide intense and normal illumination respectively and a hand-held instrument having a pinhole through which the person to be tested may view the illuminated line of indicia and means for positioning the person to be tested for near vision potential at the desired distance from the device.

13. A device according to claim 12 wherein the lines of indicia are lines of letters.

14. A device according to claim 13 wherein each of the lines of letters comprising a line having a letter recognition average of at least 85%.

15. A device according to claim 12 wherein the material is a thin transparent film.

16. A device according to claim 12 wherein the means for turning one of the rollers comprises automated means.

17. A method for testing the near vision potential of a human which comprises placing the person whose near vision potential is to be tested in front of an enclosure containing two transparent areas through one surface, two pairs of rollers, one pair of which is disposed within the upper part of the enclosure and the second pair of which is disposed within the lower part of the enclosure, means for turning one of the rollers, a length of material fitted around the two pairs of rollers in snug engagement therewith so that by operating the means for turning one of the rollers the material moves around the two pairs of rollers, said material having a series of vision testing lines of indicia sized to test near visual acuity from 20/20 to 20/200, each of said lines being visible through one area and each of said lines having on the material and visible through the other area markings from 20/20 to 20/200 which is visible to the person conducting the test thereby indicating the line which is visible to the person being tested, two sources of illumination disposed within the enclosure one of which is intense, the source of the intense illumination is disposed in a position to illuminate the line of indicia and the other source is positioned to illuminate the series of numbers from 20/20 to 20/200, and having means for providing sufficient energy to the illumination sources to enable them to provide intense and normal illumination respectively, providing the person to be tested with a hand-held instrument having a pinhole through which the person to be tested will view the intensely illuminated lines of indicia and which has means for positioning the person whose near vision potential is to be tested at the desired distance from the device, positioning the patient the proper distance from the device to test near vision potential by using the means for positioning the person, illuminating the two sources of illumination, and using the means for turning one of the rollers to determine the person's near visual acuity while the person looks through the pinhole with each eye to be tested at the intensely illuminated indicia.

18. A method according to claim 17 wherein the lines of indicia are lines of letters.

19. A method according to claim 18 wherein each of the lines of letters comprises a line having a letter recognition average of at least 85%.

20. A method according to claim 17 wherein the material is a thin transparent film.

21. A method according to claim 17 wherein the means for turning one of the rollers comprises automated means.

22. A method according to claim 17 for determining the vision potential for a person having a cataract in at least one eye.

* * * * *